United States Patent [19]

Berg et al.

[11] 4,213,909

[45] * Jul. 22, 1980

[54] PROCESS FOR THE PREPARATION OF 1-AMINO-4-BROMOANTHRAQUINONE-2-SULFONIC ACID II

[75] Inventors: Gerhard Berg; Walter Hohmann, both of Leverkusen; Karl-Julius Reubke, Cologne; Klaus Wunderlich, Leverkusen, all of Fed. Rep. of Germany

[73] Assignee: Bayer Aktiengesellschaft, Leverkusen, Fed. Rep. of Germany

[*] Notice: The portion of the term of this patent subsequent to Jul. 22, 1997, has been disclaimed.

[21] Appl. No.: 939,714

[22] Filed: Sep. 5, 1978

[30] Foreign Application Priority Data

Sep. 10, 1977 [DE] Fed. Rep. of Germany ....... 2740889

[51] Int. Cl.$^2$ ............................................. C07C 143/63
[52] U.S. Cl. ................................................... 260/371
[58] Field of Search .................... 260/371, 378, 381

[56] References Cited

U.S. PATENT DOCUMENTS

| | | | |
|---|---|---|---|
| 1,841,997 | 1/1932 | Weinland | 260/371 |
| 2,413,790 | 1/1947 | Seymour et al. | 260/371 |
| 2,874,168 | 2/1959 | Graham et al. | 260/378 |
| 3,931,253 | 1/1976 | Krenmueller et al. | 260/378 |
| 4,021,456 | 5/1977 | Seha | 260/381 |

FOREIGN PATENT DOCUMENTS

| | | | |
|---|---|---|---|
| 5459 | of 1901 | United Kingdom | 260/371 |
| 1291225 | 10/1972 | United Kingdom | 260/371 |

OTHER PUBLICATIONS

*Chemical Abstract* vol. 82, #31183; "1–Amino–4––bromoanthraquinone", Nakahara, 7/24/74.

*Primary Examiner*—Patrick Garvin
*Assistant Examiner*—Raymond K. Covington
*Attorney, Agent, or Firm*—Sprung, Felfe, Horn, Lynch & Kramer

[57] ABSTRACT

A process for the preparation of 1-amino-4-bromoanthraquinone-2-sulfonic acid or an alkali metal salt thereof by converting 1-aminoanthraquinone (which can be obtained by reduction of 1-nitroanthraquinone with sodium sulfide and/or sodium bisulfide or reaction of the 1-nitroanthraquinone with ammonia) by contacting the same with oleum at a temperature in the range of 90° to 150° C. optionally in the presence of an alkali metal sulfate and thereafter treating the so-sulfonated composition with bromine at a temperature in the range of from 60° to 100° C. 1-amino-4-bromoanthraquinone-2-sulfonic acid or an alkali metal salt thereof can be precipitated from the reaction mixture either by adjusting the sulfuric acid concentration thereof to 60 to 85 percent by weight or by stirring the reaction mixture into water, which optionally contains an alkali metal sulfate.

14 Claims, No Drawings

PROCESS FOR THE PREPARATION OF 1-AMINO-4-BROMOANTHRAQUINONE-2-SULFONIC ACID II

CROSS-REFERENCE TO RELATED APPLICATION

This application is related to application Ser. No. 939,715 filed concurrently herewith, of Dr. Muders, Dr. Leister, Dr. Dittmer, H. Schönhagen, with title: Process for the preparation of 1-amino-4-bromoanthraquinone-2-sulphonic acid I.

The present invention relates to a process for the preparation of 1-amino-4-bromoanthraquinone-2-sulphonic acid, or alkali metal salts thereof, from 1-nitroanthraquinone, which may be impure.

The preparation of 1-amino-4-bromoanthraquinone-2-sulphonic acid (designated bromamine-acid in the following text) is usually carried out in a 2-stage process, the sulphonation of 1-amino-anthraquinone with chlorosulphonic acid in a water-immiscible inert organic solvent being effected in stage 1. After separating off the organic solvent, bromination is then carried out in a neutral aqueous solution (compare, for example, U.S. Pat. No. 3,428,659) or in a solution containing sulphuric acid (compare, for example, Japanese Laid-Open Specification No. 49,076,848).

Another two-stage route consists in first sulphonating 1-amino-anthraquinone in $SO_3$-containing sulphuric acid (oleum) (compare German Nos. 263,395 and 484,997), isolating the resulting 1-amino-anthraquinone-2-sulphonic acid and brominating this compound in an aqueous medium (compare, for example, FIAT 1,313 II, page 214, U.S. Patent Nos. 2,413,790, 2,440,760 and 2,503,254 and German No. 2,303,246).

According to the process described in German No. 2,551,767, boric acid is also added during the sulphonation: The bromination is carried out in very dilute aqueous sulphuric acid.

In the processes mentioned, the aminosulphonic acid must be intermediately isolated or the sulphonation melt must be greatly diluted with water before the bromination.

In order to be able to obtain by these processes the bromamine-acid in a quality which can be used for the production of dyestuffs, it is necessary to use 1-aminoanthraquinone which is as pure as possible as the starting material (compare, for example, German No. 2,206,960 and Org. Poluprod. i. Krasiteli, Moscow, 1969, No. 4, page 70–79).

It has been found, surprisingly, that 1-amino 4-bromoanthraquinone-2-sulphonic acid, or alkali metal salts thereof, is obtained in high yield and good quality when (a) 1-nitroanthraquinone, which may be impure, is converted into 1-aminoanthraquinone by reduction with sodium sulphide and/or sodium bisulphide or by replacing the nitro group using ammonia under pressure, then (b) the crude 1-amino-anthraquinone is first treated with oleum at temperatures in the range from 90° to 150° C., optionally in the presence of an alkali metal sulphate and the product is then treated with bromine at temperatures in the range from 60° to 100° C., and thereafter (c) the 1-amino-4-bromoanthraquinone-2-sulphonic acid, or alkali metal salts thereof, is precipitated from the reaction mixture by adjusting the sulphuric acid concentration to a sulphuric acid content of 60 to 85% by weight or by stirring the reaction mixture into water, which optionally contains alkali metal sulphate, and is filtered off and the 1-amino-4-bromoanthraquinone-2-sulphonic acid, or alkali metal salts thereof, is appropriately redissolved in water and reprecipitated.

It is not necessary to use pure 1-nitroanthraquinone or 1-aminoanthraquinone as the starting material in the process according to the invention. Rather, it is one of the characteristics of the process according to the invention to employ impure 1-nitroanthraquinone. Such an impure 1-nitroanthraquinone which has a pure content of 1-nitroanthaquinone of about 70 to 90% is suitable as the starting material.

The crude 1-nitroanthraquinone to be employed can in itself be obtained by any desired processes, as long as it fulfils the abovementioned purity requirements. It can be obtained, for example, by the processes described in German No. 2,039,822. However, a 1-nitroanthraquinone which is obtained by the nitration instructions of Examples 1c, 2c or 3c or by the processes described in German No. 2,233,185 is preferably employed. The 1-nitroanthraquinone thus prepared contains about 70 to 80%, preferably 72 to 77%, of 1-nitroanthaquinone, about 5 to 10%, preferably 6 to 8%, of $\alpha,\alpha$-dinitroanthaquinones, in each case, say, about 4 to 10%, preferably 5 to 8%, of $\alpha,\beta$-dinitroanthaquinones and 2-nitroanthraquinone and less than 5%, preferably less than 3%, of anthraquinone.

The nitroanthraquinone mixtures can be converted into corresponding amine mixtures in process step (a) by processes which are in themselves known, for example by treatment with reducing agents or by replacing the nitro group by means of ammonia.

The reduction of the nitro group can be carried out, for example, with catalytically activated hydrogen or with hydrazine hydrate, but preferably with sodium sulphide and/or sodium bisulphide (compare, for example, German Nos. 2,340,114, 2,425,814, 2,348,102 and 2,164,304 and U.S. Pat. No. 2,874,168).

Replacement of the nitro group by the amino group can be effected by the action of ammonia or salts of ammonia in water and/or in the presence of inert organic solvents, acid-trapping substances, such as sodium carbonate or alkali metal bicarbonates, appropriately being added, at elevated temperature and preferably under pressure (compare, for example, German Published Nos. 2,211,411, 2,409,542 and 2,526,657).

If the nitro group replacement is carried out in water, an amine mixture is obtained, the composition of which essentially corresponds to the composition of the nitroanthraquinone mixture, taking into consideration the stoichiometry.

However, one can also carry out the reduction in a manner such that a partially purified 1-amino-anthraquinone is formed, such as is described in Examples 3 and 5 for solvent treatment at the amine stage or sulphite treatment at the nitro stage. In practice, such pre-purifications can be carried out in the course of the necessary reaction steps of the claimed process without appreciable additional expense. However, a pre-purification of this type is not essential to the invention, since good yields and qualitites of bromamine-acid can also be obtained without an operation of this type.

On the other hand, an increased content in the particular mixture of nitroanthraquinone or aminoanthraquinone which results from a treatment of this type can facilitate the later isolation of the bromamine-acid. A high 1-nitroanthraquinone content in the 1-nitroanthraquinone mixture to be employed can be easily obtained, for example, by pre-purifying the nitroanthraquinone mixtures obtained in a mixed acid nitration, for example using solvents as described in Example 4.

According to process step (b), the 1-amino-anthraquinone mixture obtained according to (a) is treated in about 4 to 40% strength oleum, preferably in 10 to 25% strength oleum, optionally in the presence of an alkali metal sulfate, at temperatures in the range from 90° to 150° C., preferably at 100° to 140° C.

The alkali metal salt addition is intended to prevent not only the entry of a further sulphonic acid group, but also hydroxylation with 4-position. Anhydrous sulphates are preferably used.

In general, 0.1 to 1.4 parts, preferably 0.4 to 1.2 parts, of alkali metal sulphate per part of aminoanthraquinones are added to the reaction mixture.

Of oleum, about 2 times to 8 times, preferably 2 times to 4 times, the amount by weight of oleum, relative to aminoanthraquinones, are added to the mixture obtained according to step (a). The amount of oleum, the $SO_3$ content of the oleum and the reaction temperature have a particular relationship here. Preferably, low $SO_3$ contents are combined with high amounts of oleum and average to high temperatures, and high $SO_3$ contents are combined with low amounts of oleum at low to average temperatures.

In general, about 1 to 10 hours, preferably 2 to 6 hours, are required for the sulphonation. The mixture obtained according to step (a) is thus virtually completely converted into a mixture consisting of predominantly 1-aminoanthraquinone-2-sulphonic acid and 1-amino-anthraquinone-2,4-disulphonic acid. The latter is formed chiefly in the final phase of the sulphonation, in which the formation of the 1-aminoanthraquinone-2-sulphonic acid only continues to proceed slowly. The formation of the 2,4-disulphonic acid is not critical for the further course of the reaction because this compound is quite substantially converted into bromamine-acid during the subsequent bromination. However, since 1-amino-2,4-dibromo-anthraquinone and 1-amino-2-bromo-anthraquinone-4-sulphonic acid also form to a small extent, it is advisable not to carry out the sulphonation until the aminoanthraquinone has completely disappeared, but to discontinue it when only about 1 to 5%, preferably 2 to 3%, of aminoanthraquinone can be detected in the mixture. As can be shown by chromatography, the diaminoanthraquinones present and the 2-amino-anthraquinone are converted into various brominated monosulphonic acid and disulphonic acid derivatives during the sulphonation.

The bromination of the anthraquinonesulphonic acids is carried out in the mixture directly after the sulphonation, without prior dilution with water, by the action of bromine at temperatures in the range from about 60° to 100° C., preferably at 70° to 90° C. The reaction mixture must be cooled to these temperatures before adding the bromine.

It is advantageous for the bromination to add a customary halogenation catalyst, such as iodine. However, the addition of such a catalyst is not absolutely necessary for the process according to the invention.

Since a large proportion of the hydrogen bromide formed during the bromination is reoxidized to bromine in the reaction mixture, less than 1 molar equivalent of bromine is consumed per mol of 1-aminoanthraquinone employed. At least 0.5 molar equivalent, in general about 0.6 to 0.9 molar equivalent, of bromine, and preferably 0.6 to 0.7 molar equivalent of bromine, relative to 1 mol of 1-amino-anthraquinone, is required.

The bromination can be carried out under normal pressure with reflux cooling, or under pressure. It is advantageously carried out under normal pressure, but sometimes it can be favorable to carry it out under a pressure of up to about 6 bars.

The course of the bromination can be readily followed by chromatography. In the preferred temperature range, the bromination has ended after about 4 to 16 hours. Before the working up it is appropriate to strip off excess bromine in vacuo, in order to avoid on the one hand odor nuisances and on the other hand side reactions by the action of bromine in the presence of water.

The bromamine-acid, or alkali metal salts thereof, can be isolated according to process step (c) in various manners.

In the first case, the reaction mixture, appropriately after prior addition of sulphuric acid of various concentrations (about 30–70% strength by weight sulphuric acid) or after careful dropwise addition of water, can be added to initially introduced water or ice-water, whilst stirring. The bromamine-acid, which still contains by-products, can then be isolated from the acid suspension by filtration, if appropriate, after adding alkali metal salts. In addition to about 2 to 5% of non-sulphonated amino-anthraquinones, such as 1-amino-2- and -4-bromo-anthraquinone and 1-amino-2,4-dibromo-anthaquinone, the crude bromamine-acid thus obtained contains about 1% of 1-amino-anthraquinone-2-sulphonic acid and a larger amount (about 3–10%) of a mixture of other brominated aminoanthraquinone-sulphonic acid derivatives.

Clarification in an acid medium, for example at pH 3, or an alkaline clarification, for example at pH 9, has proven suitable for separating off the water-insoluble amino-anthraquinones. The clarification is advantageously effected in the presence of active charcoal and/or silica gel. The bromamine-acid can be precipitated out of the filtrate of the clarification in the form of its alkali metal salt by salting out, for example with sodium chloride and/or potassium chloride or sodium sulphate and/or potassium sulphate. The alkali metal salt is isolated, for example by filtration in a suction filter, and the filter cake is washed with dilute salt solution (about 1 to 5% strength) and dried. A quite predominant proportion of the brominated sulphonation products which originate from the impurities of the crude 1-amino-anthraquinone remain in the filtrate. The resulting alkali metal salt of bromamine-acid has a high purity ($>90\%$). The salt of bromamine-acid contains only about 1% of non-sulphonated aminoanthraquinones, about 1% of 1-amino-anthraquinone-2-sulphonic acid and about 0.5 to 2% of other (brominated) aminoanthraquinone-sulphonic acid derivatives as impurities. The deficit to make up to 100% consists of alkali metal salts and/or water. The bromamine-acid proportion relative to the proportion of organic compounds is over 95%.

A further working up method for the bromamine-acid can be carried out as follows.

The bromamine-acid melt is diluted by adding water or dilute aqueous sulphuric acid such that an approximately 60 to 85% strength by weight, preferably 65 to 80% strength by weight, sulphuric acid is formed, the precipitated sulphate of bromamine-acid is filtered off and the mother liquor is driven out of the filter cake by washing with dilute aqueous sulphuric acid ($H_2SO_4$ content > 30%, preferably > 50%). The sulphate of bromamine-acid, which has been washed with sulphuric acid, is hydrolysed by washing with water and/or sulphate-containing water, the sulphuric acid is removed and the bromamine-acid is then dried.

A pure form of bromamine-acid which is particularly easy to filter is obtained if the dilution is carried out such that the bromamine-acid melt is metered into initially introduced dilute sulphuric acid (preferably with a $H_2SO_4$ content of 20-40%). Dilution with water or water-containing sulphuric acid is carried out at elevated temperature, preferably at about 70° to 100° C., and the filtration is carried out at about 30° to 70° C.

The dilution can be carried out within about ½ to 3 hours, preferably within 1 to 2 hours. Before the filtration it is appropriate to subsequently stir the mixture at the filtration temperature for about ½ to 10 hours.

The filtration temperature and the subsequent stirring times depend on the nature and amount of the by-products.

The rule which can be applied is that the more impurities are present, the more the filtration temperature must be increased within the range indicated. As the impurities increase—the crystallisation equilibrium for the bromamine-acid is established more slowly—longer subsequent stirring times within the period indicated are frequently necessary.

In general, a bromamine-acid quality which corresponds to that of the working up variant first described is obtained. In the case of bromamine-acid which is difficult to filtrate or wash out, it can be that the quality is only achieved if the filtration and washing are followed by redissolving and reprecipitation in the manner first described.

The bromamine-acid is obtained in a yield of about 65 to about 80% of theory, relative to 1-nitro-anthraquinone, by the process according to the invention. In this process, the bromamine-acid is obtained in a purity of about 80 to 90%, preferably 83 to 86%, based on the molecular weight: 382. Its proportion of organic substance is over 95%.

Compared with known processes, the process according to the invention is distinguished by the following advantages: the process according to the invention can be carried out starting from impure 1-nitro-anthraquinone. In this procedure, 1-nitro-anthraquinone can be employed, without further purification, in the form in which it is obtained in a mononitration by precipitation of all the anthraquinone constituents.

Furthermore, 1-amino-anthraquinone can be employed, without further purification, in the form in which it is obtained in the reduction or the nitro/amino group exchange of the crude 1-nitro-anthraquinone.

In addition, it is an exceptional advantage that the bromamine-acid can be prepared from the crude 1-amino-anthraquinone mixture by sulphonation and bromination without further isolation of the intermediate products (one-pot process). The process according to the invention thereby proves to be particularly economical.

In addition, the isolation of the bromamine-acid can be carried out without pollution of the environment and economically, since the bromamine-acid can be isolated from concentrated (70 to 90% strength by weight) sulphuric acid. It is thereby possible either to regenerate the sulphuric acid from the mother liquors by suitable measures, for example in a Plinke installation, without large amounts of water having to be distilled off, or to re-use some or all of the mother liquors, together with the dissolved impurities and after prior concentration by means of oleum, as the sulphuric acid for the reaction. Effluent problems then no longer occur or occur only to a minor extent.

Bromamine-acid is an important intermediate product for numerous valuable anthraquinone dyestuffs, compare Colour Index 62,125, 62,130 and 62,070.

The examples which follow are intended to illustrate the invention in more detail. In the examples, unless expressly indicated otherwise, parts denote parts by weight. The content data are based on a determination of organically bonded bromine in combination with quantitative column chromatography and thin layer chromatography.

EXAMPLE 1

(a) 45 g of 1-amino-anthraquinone (content: 72.5%) are introduced into a mixture consisting of 80 ml of oleum (20% strength) and 40 g of anhydrous $Na_2SO_4$ in the course of ½ hour. The temperature thereby rises to 130° C. The mixture is kept at this temperature until less than 3% of 1-amino-anthraquinone can be detected in a sample which is removed (about 4-5 hours are required). The mixture is then cooled to room temperature, 1 g of finely powdered iodine is added, 8 ml of bromine are added dropwise at room temperature in the course of 30 minutes and the mixture is warmed to 80° C. in the course of 30 minutes and kept at this temperature until only traces of 1-amino-anthraquinone-2-sulphonic acid can be detected in a sample which is removed (about 7-10 hours are required).

Excess bromine is now stripped off in vacuo and the reaction mixture which remains is stirred into 2 l of water. 320 g of $Na_2SO_4$ are added in portions to the solution and the mixture is stirred at room temperature for 2 hours. The precipitate is filtered off and washed with 10% strength $Na_2SO_4$ solution until almost neutral. In order to separate off the non-sulphonated aminoanthraquinone constituents, the material on the filter is stirred in 800 ml of water at 95° C., 4 g of active charcoal are added, the pH is adjusted to 9-10 by adding sodium carbonate and the mixture is filtered at 90° C. The Na salt of the bromamine-acid is salted out of the clarified filtrate with 20 g of $Na_2SO_4$, the mixture is stirred in the cold overnight and the product is filtered off, washed with 1% strength $Na_2SO_4$ solution and dried.

45 g of bromamine-acid are obtained, giving the following analysis:

[The analysis figures relate here and in the following text to the free sulphonic acids (even when the alkali metal salts thereof are present)].

84.1% of 1-amino-4-bromo-anthraquinone-2-sulphonic acid, 1.4% of non-sulphonated aminoanthraquinones, 1.0% of 1-aminoanthraquinone-2-sulphonic acid, 0.9% of other anthraquinonesulphonic acids and 7.0% of water.

The yield is accordingly 72% of theory.

(b) The 1-amino-anthraquinone employed in (a) was obtained as follows:

750 ml of water and 324 g of $Na_2S.9H_2O$ are heated to 90°-95° C. in a cylindrical reaction vessel (1.5 l capacity, diameter 10 cm, height 20 cm) with a lid fitted with three tubes, which is provided with an anchor stirrer (diameter 9 cm, anchor height 12 cm) and thermometer, 81 g of finely sieved 1-nitro-anthraquinone (content 73.9%) is then stirred in at the same temperature in the course of one hour and finally the mixture is subsequently stirred at 90°–95° C. for 30 minutes. The reaction mixture is filtered and the residue is washed with hot water until neutral and dried at 60° C. in vacuo. 71.3 g of crude 1-amino-anthraquinone of the following composition are obtained: 72.5% of 1-amino-anthraquinone=98% of theory, 3.1% of 1,5-diamino-anthraquinone, 2.8% of 1,8-diamino-anthraquinone, 3.0% of 1,6-diamino-anthraquinone, 3.1% of 1,7-diaminoanthraquinone, 2.3% of anthraquinone, 5.9% of 2-amino-anthraquinone and 0.1% of 2,6-+2,7-diamino-anthraquinone.

(c) The 1-nitro-anthraquinone employed in (b) was obtained as follows:

150 g of a nitration mixture in which the reaction has ended and which contains 68 g of crude 1-nitroanthraquinone are initially introduced into a cylindrical reaction vessel (1.5 l capacity, diameter 10 cm, height 20 cm) with a lid fitted with 4 tubes, provided with an anchor stirrer (diameter 9 cm, anchor height 12 cm) thermometer, condenser and dropping funnel. 500 g of technical grade anthraquinone (99% pure) and 890 g of mixed acid of the following composition: 351 g of $H_2SO_4$ (100% pure), 464 g of $HNO_3$ (100% pure) and 76.5 g of $H_2O$, are uniformly introduced into this receiver separately, but with synchronous metering, at 48°–50° C. and at a stirring speed of 200 revolutions/minute in the course of 3 hours. A temperature of 49°–51° C. is thereby established. After 10–20% of the starting materials have been introduced, a two-phase system forms which exhibits a great tendency to demix. It consists of a specifically heavier, liquid, clear, inorganic phase consisting of mixed acid, in which small proportions of anthraquinone and nitrated anthraquinone are dissolved, and a specifically lighter, also completely or predominantly liquid, organic phase consisting of anthraquinone, nitroanthraquinone, nitric acid and small proportions of sulphuric acid. This two-phase system remains in existence throughout the entire metering time.

After the metering has ended, the mixture is subsequently stirred at 50° C. for one hour and finally at 60° C. for 3 hours. The liquid organic phase thereby gradually passes over into a solid phase with an increasing degree of nitration of the anthraquinone, whereupon a progressive thickening of the mixture is to be observed, but it remains easily stirrable until the end of the reaction.

The mixture is stirred into 5 l of cold water, subsequently stirred at 60° C. for ½ hour and filtered and the residue is washed with hot water until neutral and dried in vacuo at 120° C. The yield of product thus obtained is 685 g. Composition: 1.9% of anthraquinone, 73.9% of 1-nitroanthraquinone, 8.0% of 2-nitro-anthraquinone, 3.2% of 1,6-dinitro-anthraquinone, 3.4% of 1,7-dinitro-anthraquinone, 3.6% of 1,5-dinitro-anthraquinone, 3.4% of 1,8-dinitro-anthraquinone and 0.2% of 2,6-+2,7-dinitro-anthraquinone.

The yield of 1-nitro-anthraquinone is 75% of theory.

EXAMPLE 2

(a) 10 l of oleum (20% strength) are initially introduced into a 50 l kettle and 5 kg of anhydrous sodium sulphate and 7.5 kg of 1-amino-anthraquinone (74.3% pure) are successively introduced and the mixture is heated to 130° C. in the course of 1 hour, whilst stirring, and kept at the same temperature for 2 hours. 2.25 kg of anhydrous sodium sulphate and 5.5 kg of oleum (20% strength) are now successively introduced and the mixture is subsequently stirred until less than 3% of non-sulphonated starting material can be detected in a sample which is removed (about 3–4 hours are required). The mixture is now cooled to 80° C., 10 g of iodine are added, a total of 3,000 g of bromine are introduced in portions at this temperature in the course of 8 hours and the mixture is kept at this temperature until <2% of amine-acid can be detected in a sample which is removed.

The melt is now cooled to 50° C. and diluted with 10 l of water at 50°–60° C. in the course of one hour, the mixture is subsequently stirred at 50°–60° C. for a further hour and forced into a filter press and the residue is rinsed with a total of 20 l of $H_2SO_4$ (60% strength) in portions. The filter cake is mixed with 100 l of water, the mixture is heated to 90° C., kept at 90° C. for 30 minutes, cooled to 30°–40° C. and kept there for 30 minutes and pressed off and the residue is washed with 100 l of cold 1.3% strength sodium sulphate solution and dried.

8.19 kg of bromamine-acid are obtained having the composition: 85.1% of 1-amino-4-bromo-anthraquinone-2-sulphonic acid, 0.8% of non-sulphonated 1-amino-anthraquinones, 1.1% of 1-amino-anthraquinone-2-sulphonic acid and 1.0% of other anthraquinonesulphonic acids.

The yield is accordingly 73% of theory.

(b) The 1-amino-anthraquinone employed in (a) was obtained as follows:

54 kg of 1-nitro-anthraquinone (75.6% pure) was introduced into a mixture of 50 l of water and 27 kg of NaSH solution (18.5% strength) at 90° C. in the course of 1 hour, whilst stirring, and the mixture is stirred at 90°–95° C. for a further ½ hour. The reaction mixture is filtered hot and the residue is washed with 1% strength sodium hydroxide solution and finally with hot water until neutral and dried.

46.3 kg of 1-amino-anthraquinone of the following composition are obtained: 74.3% of 1-amino-anthraquinone=95.6% of theory, 3.3% of anthraquinone, 4.8% of 2-amino-anthraquinone, 3.2% of 1,5-diamino-anthraquinone, 2.9% of 1,8-diamino-anthraquinone, 3.6% of 1,6-diamino-anthraquinone, 3.6% of 1,7-diamino-anthraquinone and 0.5% of 2,6-+2,7-diamino-anthraquinone=96.2%.

Instead of 27 kg of NaSH solution (18.5% strength), it is also possible to employ a mixture of 9.8 kg of $Na_2S.9H_2O$ and 12.8 kg of NaSH solution (18.5% strength).

(c) The 1-nitro-anthraquinone employed in (b) was obtained as follows:

10,000 g of anthraquinone (99% pure) and 16,100 g of mixed acid (composition: 52.1% of $HNO_3$ (100% pure), 39.3% of $H_2SO_4$ (100% pure) and 8.6% of $H_2O$) per hour are metered synchronously at 48°–50° C., whilst stirring vigorously, into the first element of a four-stage cascade (three-stage reaction cascade+dilution cascade) which has a capacity of 35 l in each case and is provided with a charging screw and mixed acid metering pump on cascade 1, a water metering pump on cascade 4 and water jackets which can be heated and cooled on cascades 1–4. The washing 1 from the filtration of the 1-nitro-anthraquinone obtained (about 18,900 g/hour) is simultaneously metered synchronously into cascade 4.

The temperature in the individual elements of the cascade are adjusted as follows: cascade 1: 48°–50° C., cascade 2: 54°–56° C., cascade 3: 59°–61° C. and cascade 4: 58°–62° C.

The working up is carried out in a manner such that the overflow from cascade 4 is continuously filtered on a rotary filter, and the material on the filter is washed with water at 60° in 2 different zones. 17,900 g of water per hour are fed into the first zone, and the filtrate thereby obtainable (washing 1), which is obtained in an amount of about 18,900 g/hour, is used for dilution in cascade 4. 12,400 g of water per hour are fed into the second zone. The filtrate thereby obtainable (washing 2) can be fed to the biological processing of the effluent.

The material on the filter, which has been washed until neutral, is dried thoroughly in vacuo. 12,550 g of product of the following composition are obtained per hour: 2.0% of anthraquinone, 6.7% of 2-nitro-anthraquinone, 75.6% of 1-nitro-anthraquinone, 3.0% of 1,6-dinitro-anthraquinone, 3.8% of 1,7-dinitro-anthraquinone, 3.8% of 1,5-dinitro-anthraquinone, 3.4% of 1,8-dinitro-anthraquinone, 0.6% of 2,7-+2,6-dinitro-anthraquinone and 1.1% of other substances.

The yield from 1-nitro-anthraquinones is 77.9% of theory.

EXAMPLE 3

(a) 60 g of sodium sulphate are stirred into 120 ml of oleum (20% strength) below 80° C., 90 g of 1-amino-anthraquinone (87.5% pure) are then introduced at 50° to 80° C. and the mixture is warmed to 130° C. in the course of 30 minutes and kept at this temperature for 2 hours. 50 ml of oleum (30% strength) and 33 g of sodium sulphate are now added and the mixture is kept at 130° C. for a further 5 hours. Less than only 4% of 1-amino-anthraquinone can still be detected by chromatography.

The mixture is cooled to 80° C. and 0.2 g of very finely divided iodine and a total of 11.6 ml of bromine are added at a uniform rate at 80° C. in the course of about 7 hours: less than only 2% of amine-acid can now still be detected by chromatography.

Excess bromine is now stripped off in vacuo, the mixture is added to 4 l of water, whilst stirring, 640 g of $Na_2SO_4$ are added, the mixture is subsequently stirred at room temperature for 2 hours and filtered off and the residue is washed with 200 ml of 10% strength $Na_2SO_4$ solution and thoroughly pressed off. 327 g of filter cake are obtained. The filter cake is taken up in 1,200 ml of purified water, the pH is adjusted to 9 with sodium hydroxide solution and, after adding 8 g of active charcoal and 8 g of kieselguhr, the mixture is warmed to 95° C. for 20 minutes, whilst stirring. It is filtered and the residue is washed with 240 ml of hot purified water of 95° C. 1,610 ml of filtrate and, after drying, 18.4 g of residue are obtained. The filtrate is salted out with 120 g of $Na_2SO_4$ at 80° C., the mixture is subsequently stirred at the same temperature for 1 hour, cooled to 30° C. and filtered and the residue is washed with 300 ml of 1.5% strength $Na_2SO_4$ solution and dried.

126.6 g of the Na salt of bromamine-acid are obtained with a purity of 84.4% (relative to the free acid).

(b) The 1-amino-anthraquinone employed in (a) was obtained as follows:

145 g of crude 1-nitro-anthraquinone (75.1% pure), 145 g of nitrobenzene and 145 g of water are heated to 190° C. in a 1.3 l stirred autoclave. A solution of 19.7 g of $NH_3$, 38 g of $Na_2CO_3$, 15.7 g of $NaHCO_3$ and 200 g of water is pumped in over a period of ½ hour. The mixture is allowed to react at 190° C. for a further 15 minutes and the heavy organic phase is forced out of the autoclave into a crystallisation vessel. After cooling, the solid is filtered off and dried.

Yield: 86 g of 87.5% pure 1-amino-anthraquinone ≙ 78.4% of theory.

Impurities: 2.8% of anthraquinone, 1.8% of 1-nitro-anthraquinone, 3.7% of 1-amino-5-nitro-anthraquinone, 1.1% of 1,5-diamino-anthraquinone and 1.0% of 1,8-diamino-anthraquinone.

(c) The 1-nitro-anthraquinone employed in (b) was obtained as follows:

280 g of $H_2SO_4$ (78% strength) are initially introduced into a cylindrical reaction vessel, 200 g of anthraquinone are stirred into this acid and 235 g of $NHO_3$ (98% strength) are added dropwise in the course of 30 minutes, whilst stirring. The temperature thereby increases to 47° C. A mixture of 137 g of $H_2SO_4$ (96% strength) and 235 g of $HNO_3$ (98% strength) is then added dropwise at a uniform rate in the course of one hour, and 300 g of anthraquinone are added at a uniform rate during the addition of the last 75% of the mixed acid. A temperature of 50°–52° C. is thereby maintained. The mixture is subsequently stirred at 50° C. for one hour and at 60° C. for 2 hours. After working up analogously to Example 1c, 619 g of a 1-nitro-anthraquinone mixture of the following composition are obtained: 1.5% of anthraquinone, 8.2% of 2-nitro-anthraquinone, 75.1% of 1-nitro-anthraquinone, 3.0% of 1,6-dinitro-anthraquinone, 2.9% of 1,7-dinitro-anthraquinone, 3.7% of 1,5-dinitro-anthraquinone and 2.9% of 1,8-dinitro-anthraquinone.

The yield of 1-nitro-anthraquinone is 76.6% of theory.

EXAMPLE 4

(a) The reaction is carried out as described in Example 3, but 86.8% pure 1-amino-anthraquinone is employed.

The melt, which has been freed from excess bromine, is stirred into 900 ml of ice-water; the temperature thereby rises to 30° C. After 30 minutes at this temperature, the solid is filtered off and thoroughly pressed off. The filter cake (262 g) is taken up in 1,200 ml of purified water, the pH is adjusted to 7 with NaOH and then to 9 with sodium carbonate, 6 g of active charcoal and 10 g of kieselguhr are added, the mixture is warmed to 95° C., subsequently stirred at this temperature for 20 minutes and filtered and the residue is washed with 240 ml of $H_2O$ of 95°° C. 1,605 ml of filtrate and, after drying, 19.2 g of residue are obtained.

160 g of $Na_2SO_4$ are added to the filtrate at 80° C., the mixture is subsequently stirred at 80° C. for 1 hour, cooled to 30° C. and filtered and the residue is washed with 300 ml of 1.5% strength $Na_2SO_4$ solution and dried.

128.6 g of the Na salt of bromamines-acid are obtained with a purity of 85.2% (calculated relative to the free acid).

(b) the 1-amino-anthraquinone employed in (a) was obtained as follows:

85 g of 1-nitro-anthraquinone, redissolved in nitrobenzene and reprecipitated (88.2% pure), is heated to 180° C. with 145 ml of water in a 0.7 l stirred autoclave. A solution of 14.6 g of $NH_4Cl$ in 240 ml of 25% strength $NH_3$ solution is pumped in over a period of 5 minutes. The mixture is allowed to react for a further hour and cooled and the product is filtered off. After drying, 75.4 g of 86.8% pure 1-amino-anthraquinone ≙ 97.4% of theory are obtained.

(c) The 1-nitro-anthraquinone employed in (b) was obtained as follows:

(1) Purification of the nitroanthraquinone mixture with nitrobenzene in order to obtain with washing filtrate 100 g of 1-nitro-anthaquinone of the following composition: 3.41% of anthraquinone, 7.18% of 2-nitroanthraquinone, 72.6% of 1-nitro-anthraquinone, 4.09% of 1,6-dinitro-anthraquinone, 3.80% of 1,7-dinitroanthraquinone, 3.19% of 1,5-dinitro-anthraquinone, 3.07% of 1,8-dinitro-anthraquinone and 0.12% of $H_2SO_4$, obtained by the process of German No. 2,233,185, are warmed to 150°, together with 108 g of nitrobenzene, until a clear solution forms, and the solution is subsequently cooled to 65° C. in the course of 30 minutes and then stirred at 65° C. for 3 hours. The crystals are now filtered off at 65° C. and, after changing the receiver, are washed with 108 g of cold nitrobenzene (washing filtrate) and the residue is dried at 100° C.

(2) Purification of the nitroanthraquinone mixture using the washing filtrate as the solvent 100 g of 1-nitro-anthraquinone of the above composition is treated according to the instructions indicated under (1) using the washing filtrate from (1) instead of 108 g of nitrobenzene. Dry, pre-purified 1-nitroanthraquinone (crystals) and the mother liquor as well as the washing filtrate are obtained. The washing filtrates obtained according to these instructions are in each case employed as solvents for the next crystallisation mixture.

After re-using the washing filtrate twice (=3rd crystallisation), the crystallisation equilibria have been established. The following average test result was obtained in the subsequent 6 crystallisations (per 100 g of starting material of the above composition):

Crystals: 76.6 g of 88.2% pure 1-nitro-anthraquinone, corresponding to a separation yield of 93.1%.
Analysis: 0.45±0.08% of anthraquinone, 0.40±0.09% of nitroanthraquinone, 88.20±1.05% of 1-nitroanthraquinone, 0.74±0.08% of 1,6-dinitroanthraquinone, 3.16±0.19% of 1,7-dinitroanthraquinone, 3.39±0.15% of 1,5-dinitroanthraquinone, 1.16±0.19% of 1,8-dinitroanthraquinone and 0.02±0.01% of $H_2SO_4$.

EXAMPLE 5

(a) The procedure followed is as described in Example 2, but 86.7% pure 1-amino-anthraquinone is employed.

The filter cake from the filter press is worked up as follows:

It is stirred into 100 l of water, the mixture is filtered at 30°-40° C. and the residue is washed with cold water until the pH in the runnings is 2.5–3.

The material on the filter is now dissolved in the required amount of water (about 130 l are required) at 90°-95° C., 250 g each of active charcoal and silica gel are added, the mixture is filtered, the residue is rinsed with hot water, the filtrate is salted out with 3-4 kg of $Na_2SO_4$ at 30°-40° C. and the precipitate is warmed again to 80° C., stirred until cooled to 40° and filtered off.

8.9 kg of bromamine-acid, in the form of the Na salt, are obtained, having the composition: 87.7% of 1-amino-4-bromo-anthraquinone-2-sulphonic acid, 0.4% of non-sulphonated 1-amino-anthraquinones, 0.9% of 1-amino-anthraquinone-2-sulphonic acid and 1.1% of other anthraquinonesulphonic acids.

(b) The 1-amino-anthraquinone employed in (a) was obtained as follows:

100 g of 1-nitro-anthraquinone of the composition given in Example 4 (c1) are stirred in the cold in 500 ml of water for 12 hours, a solution of 75 g of $Na_2So_3$ in 200 ml of water is then added at 90° C. in the course of several hours, the mixture is kept at this temperature for a total of 8 hours, 350 g of $Na_2S.9H_2O$ are then added and the mixture is kept at this temperature until no further nitro compounds can be detected by chromatography (about 2 hours are required). The reaction mixture is filtered off hot and the residue is washed with hot water until neutral and dried.

72 g of crude 1-amino-anthraquinone are obtained having the composition: 86.7% of 1-aminoanthraquinone=86.2% of theory, 1.9% of 1,5-diaminoanthraquinone, 1.2% of 1,8-diamino-anthraquinone, 0.9% of 1,6-diamino-anthraquinone, 1.2% of 1,7-diamino-anthraquinone, 1.4% of 2-amino-anthraquinone and 2.9% of anthraquinone.

EXAMPLE 6

(a) 10 l of 20% strength oleum are initially introduced into a 50 l kettle with an anchor stirrer. There are then successively introduced 5 kg of anhydrous sodium sulphate (rise in temperature to 60°-70°) and 7.5 kg of 1-aminoanthraquinone (73.4% pure) (rise in temperature to 75° C.). The mixture is now heated to 130° in the course of 1 hour and stirred at this temperature for a further 2 hours. A further 2.25 kg of $Na_2SO_4$ and 5.5 l of 20% strength oleum are then added and the reaction is brought to completion by subsequent stirring at 130°. The end point is reached when less than only 5% of aminoanthraquinone can still be detected in a sample of the melt by thin layer chromatography. (3 to 4 hours). The mixture is then cooled to 80° and, after adding 10 g of iodine, bromination is carried out with 3.1 kg of bromine in portions. The excess bromine is blown out with nitrogen. 20 l of cold, 30% strength sulphuric acid are initially introduced into a far kettle with a capacity of 100 l. As soon as the reaction composition has cooled to a temperature of 50°-60°, the contents in the far kettle are discharged onto the mass, whereupon the temperature rises to 70°-80°. The mixture is stirred for a further 1-2 hours and pressed off at 50°-60°. The press cake is washed with 15 l of 60% strength sulphuric acid and stirred into 20 l of water and the mixture is again filtered over a press. The press cake is dissolved in 100 l of water at 80°-85° and the solution is clarified with 0.6 kg of active charcoal and 0.6 kg of silica gel. After the clarification, the bromamine-acid is precipitated at a pH of 8-9 at 80° using sodium hydroxide solution (4.7 l of 50% strength). The precipitation is brought to completion by adding 2 kg of sodium sulphate and the suspension is stirred at 80° for a further 4 hours. After cooling to 20°, it is again stirred for some time and the sodium salt of bromamine-acid is isolated via a filter press. It is washed with 100 l of 1.5% strength sodium sulphate solution. After drying, 7.5 kg of 84.8% pure bromamine-acid ≙ 67.4% of theory are obtained.

(b) The 1-aminoanthraquinone employed in (a) is obtained as in Example 2(b).

What is claimed is:

1. A process for preparing 1-amino-4-bromoanthraquinone-2-sulfonic acid or an alkali metal salt thereof which comprises:
   (a) converting 1-nitroanthraquinone to 1-aminoanthraquinone by:
      (1) contacting said 1-nitroanthrquinone with sodium sulfide and/or sodium bisulfide under reducing conditions; or
      (2) contacting said 1-nitroanthraquinone with ammonia under conditions whereby the nitro group is replaced by an amino group;
   (b) treating the product from step (a) with oleum at a temperature in the range from 90° to 150° C. optionally in the presence of an alkali metal sulfate and brominating the resultant sulfonated product with bromine at a temperature in the range from 60° to 100° C.; and
   (c) thereafter recovering 1-amino-4-bromanthraquinone-2-sulfonic acid or an alkali metal salt thereof by a process comprising:
      (1) adjusting the sulfuric acid concentration of the reaction mixture to a sulfuric acid content of 60 to 85 percent by weight; or
      (2) stirring the reaction mixture into water, which optionally contains an alkali metal sulfate.

2. A process according to claim 1 wherein the 1-nitroanthraquinone which is reacted according to step (a) contains 70 to 90 percent by weight of pure 1-nitroanthraquinone, the balance being impurities.

3. A process according to claims 1 or 2 wherein the oleum has a strength of 4 to 40 percent by weight.

4. A process according to claims 1, 2, or 3 wherein 2 to 8 times the amount by weight of oleum, relative to aminoanthraquinone, is added to the reaction mixture.

5. A process according to claims 1, 2, 3, or 4 wherein sodium sulfate and/or potassium sulfate is employed as the alkali metal sulfate.

6. A process according to claims 1, 2, 3, 4, or 5 wherein 0.1 to 1.4 parts by weight of alkali metal sulfate are employed per part by weight of aminoanthraquinone in the reaction mixture.

7. A process according to claims 1, 2, 3, 4, 5, or 6 wherein the reaction mixture is treated with at least 0.5 molar equivalent of bromine relative to 1 mol of 1-aminoanthraquinone.

8. A process according to claims 1, 2, 3, 4, 5, or 6 wherein the reaction mixture is treated with 0.6 to 0.9 molar equivalent of bromine relative to 1 mol of 1-aminoanthraquinone.

9. A process according to claim 1 wherein following the treatment of the 1-aminoanthraquinone with oleum and prior to the bromination of the sulfonated aminoanthraquinone no purification steps are performed on the reaction mixture resulting from the sulfonation.

10. A process for preparing 1-amino-4-bromoanthraquinone-2-sulfonic acid or an alkali metal salt thereof which consists essentially of:
   (a) converting 1-nitroanthraquinone to 1-aminoanthraquinone by:
      (1) contacting said 1-nitroanthrquinone with sodium sulfide and/or sodium bisulfide under reducing conditions; or
      (2) contacting said 1-nitroanthraquinone with ammonia under conditions whereby the nitro group is replaced by an amino group;
   (b) treating the product from step (a) with oleum at a temperature in the range from 90° to 150° C. optionally in the presence of an alkali metal sulfate and brominating the resultant sulfonated product with bromine at a temperature in the range from 60° to 100° C.; and
   (c) thereafter recovering 1-amino-4-bromoanthraquinone-2-sulfonic acid or an alkali metal salt thereof by a process comprising:
      (1) adjusting the sulfuric acid concentration of the reaction mixture to a sulfuric acid content of 60 to 85 percent by weight; or
      (2) stirring the reaction mixture into water, which optionally contains an alkali metal sulfate.

11. A process according to claim 1 wherein bromination is effected with a brominating agent consisting essentially of bromine.

12. A process according to claim 1 wherein step b is performed without purifying the product of step a.

13. A process according to claim 11 wherein step b is performed without purifying the product of step a.

14. A process according to claim 1 wherein the 1-amino-4-bromoanthraquinone-2-sulfonic acid or its alkali metal salt is recovered by adjusting the sulfuric acid concentration of the reaction mixture to sulfuric acid content of 60 to 85% by weight.

* * * * *